United States Patent [19]

Stacher

[11] Patent Number: 5,039,612

[45] Date of Patent: Aug. 13, 1991

[54] METHOD FOR DETECTING SURFACE OXIDATION ON TITANIUM ALUMINIDE METALLIC MATERIAL

[75] Inventor: George W. Stacher, Westminster, Calif.

[73] Assignee: Rockwell International Corporation, El Segundo, Calif.

[21] Appl. No.: 588,886

[22] Filed: Sep. 27, 1990

[51] Int. Cl.$^5$ .................. G01N 17/00; G01N 21/00
[52] U.S. Cl. ............................ 436/5; 436/6; 436/73; 436/75; 436/83; 436/164; 422/53
[58] Field of Search ................ 436/5, 6, 73, 75, 83, 436/164; 422/53

[56] References Cited

U.S. PATENT DOCUMENTS 4,551,434 11/1985 Thoma .................. 436/5

Primary Examiner—David L. Lacey
Assistant Examiner—David Redding
Attorney, Agent, or Firm—Lawrence N. Ginsberg; Charles T. Silberberg

[57] ABSTRACT

The present invention is a method of determining oxidation on a titanium aluminide material. An aqueous saturated solution of oxalic acid is prepared. The saturated solution of oxalic acid is combined with a minor portion of hydrofluoric acid solution. The resultant oxalic acid/hydrofluoric acid solution is mixed. The titanium aluminide material is immersed in the mixed solution for a sufficiently long period to allow exposure of the oxidized surface followed by inspection thereof for a white layer indicating the presence of oxidation on its surface.

6 Claims, 1 Drawing Sheet

METHOD FOR DETECTING SURFACE OXIDATION ON TITANIUM ALUMINIDE METALLIC MATERIAL

BACKGROUND OF THE INVENTION

1. Field of the Invention

This invention relates to the detection of surface oxidation on metallic materials. More particularly, this invention relates to a method for detecting surface oxidation on titanium aluminide ($Ti_3Al$) material.

2. Description of the Related Art

Oxidation of a surface of a metallic material lowers the material's mechanical properties and can result in catastrophic failure. Detection of oxidation can be determined by etching the surface. However, current chemical etch solutions/methods do not reveal oxidized surfaces on titanium aluminide materials.

U.S. Pat. No. 3,518,133, issued to W. B. Glendinning, entitled "Method for Measuring the Thickness of a Diffused Surface Layer", discloses a method for measuring the thickness of a diffused surface layer on a silicon semiconductor substrate. The Glendinning method is a multi-step method including exposing the diffused surface layer to a fine jet of corrosive vapors of hydrogen fluoride and nitrous oxide to produce a corroded portion through the diffused surface layer; washing the corroded portion out of that layer with an alkaline solution; re-exposing a layer which extends through the diffused surface layer to corrosive vapors covering the layer with an optical flat; exposing the crater and flat to monochromatic light; and counting the interference rings thus created. The Glendinning method involves removal of the diffused surface layer without a determination of the depth of the oxidized layer. Thus, the thickness of the end product cannot be adequately controlled.

U.S. Pat. No. 4,698,130, issued to J. E. Restall et al, entitled "Cleaning of Metal Articles", discloses a halide based process for the removal of surface oxidation and corrosion contamination from metallic articles especially cracked superalloy turbine components. The process utilizes a pulsed pressure cycle utilizing $CHF_3$ hydrogen and inert gas as atmosphere. The process is also applicable to etching for detection of near-surface flaws. The Restall et al method involves removal of surface contamination without detection or determination of the oxidized layer depth.

U.S. Pat. No. 4,282,266, issued to A. W. Fisher, entitled "Method for Determining Silicon Content in Layers of Aluminum and Silicon", provides a method for determining the silicon content in an aluminum film on a substrate. The substrate is immersion plated in a solution comprising the deionized water, hydrofluoric acid, and copper sulfate which plate onto the silicon in the film while etching the aluminum film. The substrate is then removed from the solution and the aluminum film visually examined to determine whether the areas plated thereon are continuous or discontinuous.

SUMMARY OF THE INVENTION

The present invention is a method of determining oxidation on a titanium aluminide material. In its broadest aspects the invention comprises the following steps: An aqueous saturated solution of oxalic acid is prepared. The saturated solution of oxalic acid is combined with a minor portion of hydrofluoric acid solution. The resultant oxalic acid/hydrofluoric acid solution is mixed. The titanium aluminide material is immersed in the mixed solution for a sufficiently long period to allow exposure of the oxidized surface. However, the immersion period is sufficiently short to prevent excessive surface etching which would obscure observation of the oxidized material. The titanium aluminide material is rinsed after immersing it. The titanium aluminide material is inspected for a white layer indicating the presence of oxidation on its surface.

Thus, in a low cost, expedient manner, detection of oxidation on titanium aluminide material is achieved. This result has been heretofore unachievable even with efforts utilizing expensive scanning electron microscope techniques and the AUGER electro-spectroscope methods.

Preferably, the step of combining the saturated solution of oxalic acid with the hydrofluoric acid solution includes combining approximately 95 parts of the saturated solution with 5 parts of about a 47–52% hydrofluoric acid solution. Oxalic dihydrate crystals may be used to form the saturated solution of oxalic acid.

The present method is particularly useful after superplastic forming/diffusion bonding processing. Such processing exposes the material to very high temperatures, i.e. approximately 1800° F., at which point oxidation could occur.

BRIEF DESCRIPTION OF THE DRAWING

The sole figure is a micrograph of a titanium aluminide panel treated in accordance with the process of the present invention, shown at a magnification of 100×.

DETAILED DESCRIPTION OF THE PREFERRED EMBODIMENTS

Figure 1:

Oxalic dihydrate crystals, such as laboratory grade crystals meeting ACS specifications, are added to distilled or deionized water until saturation is obtained. Five (5) parts of a hydrofluoric acid solution (preferably a 47–52% technical grade) are combined with 95 parts of the saturated solution of oxalic acid. These steps are conducted at room temperature.

Immediately after mixing, the etching is conducted. A standard metallographic mount of $Ti_3Al$ material is fully immersed in the oxalic acid solution mix for preferably 15 to 25 seconds. The immersion period should be sufficiently long to allow the chemical reaction between the oxalic solution and the metallic material to expose the oxidation. However, this immersion period should be sufficiently short to prevent excessive surface etching which obscures observation of the oxidized material. The material is then removed and thoroughly rinsed in water and dried. It may be observed under a microscope at an approximate magnification of 400×. A white layer on the edge of the surface of the material indicates oxidation. The depth of this layer can be determined by measurement on a micrograph.

EXAMPLE

Laboratory grade oxalic dihydrate crystals were added to distilled water until saturation was obtained. At room temperature 5 parts of a 47.0–52% technical grade hydrofluoric acid solution were combined with 95 parts of the saturated solution of oxalic acid. The resulting solution was thoroughly mixed.

A metallographic mount of titanium aluminide material of the alpha-2 class, after processing at elevated temperatures, was immersed for 15 seconds in the solution. After removal, it was rinsed in water and dried. The 100× micrograph of FIG. 1 illustrates the microstructure of the material and the presence of oxidation on the surface. The oxidation is revealed as the white layer 10. Oxidation layer 10 is approximately 0.003" thick.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A method of detecting oxidation on a titanium aluminide material, comprising the steps of:
   a) preparing an aqueous saturated solution of oxalic acid;
   b) combining said saturated solution of oxalic acid with a hydrofluoric acid solution;
   c) mixing the resultant oxalic acid/hydrofluoric acid solution;
   d) immersing a titanium aluminide material in the mixed solution to expose any oxidized surface;
   e) rinsing said titanium aluminide material after said immersion; and
   f) inspecting said titanium aluminide material to detect a white layer indicating the presence of oxidation.

2. The method of claim 1 wherein said step of combining said saturated solution of oxalic acid with said hydrofluoric acid solution comprises combining 95 parts of said saturated solution with 5 parts of a 47-52% hydrofluoric acid solution.

3. The method of claim 1 wherein said saturated solution of oxalic acid is prepared by adding oxalic dihydrate crystals to water until saturation is obtained.

4. The method of claim 1 wherein said titanium aluminide material is immersed in the mixed solution for approximately 15-25 seconds.

5. The method of claim 1 wherein said titanium aluminide material is inspected with a microscope.

6. A method of detecting oxidation on a titanium aluminide material, comprising the steps of:
   a) preparing an aqueous saturated solution of oxalic acid;
   b) combining approximately 95 parts of said saturated solution with 5 parts of approximately a 47-52% hydrofluoric acid solution;
   c) mixing the resultant oxalic acid/hydrofluoric acid solution;
   d) immersing a titanium aluminide material in the mixed solution for approximately 15-25 seconds;
   e) rinsing said titanium aluminide material after said immersion; and
   f) inspecting said titanium aluminide material with a microscope to detect for a white layer which indicates the presence of oxidation.

* * * * *